United States Patent [19]

Grier et al.

[11] 4,254,131
[45] Mar. 3, 1981

[54] TREATMENT OF PAIN, FEVER, AND INFLAMMATION WITH COMPOSITIONS CONTAINING 2-(SUBSTITUTEDPIPERIDINOMETHYL)-PROPANE AND PROPENE NITRILES

[75] Inventors: Nathaniel Grier, Englewood; Richard A. Dybas, Somerville; Bruce E. Witzel, Rahway, all of N.J.

[73] Assignee: Merck & Co., Inc., Rahway, N.J.

[21] Appl. No.: 68,376

[22] Filed: Aug. 21, 1979

[51] Int. Cl.³ .......................................... A61K 31/445
[52] U.S. Cl. .................................................. 424/267
[58] Field of Search ........................................ 424/267

[56] References Cited
PUBLICATIONS

Dybas et al., *Developments in Industrial Microbiology*, vol. 19, pp. 347–353 (1978).

*Primary Examiner*—Stanley J. Friedman
*Attorney, Agent, or Firm*—Raymond M. Speer; Mario A. Monaco

[57] ABSTRACT

A method of treating pain, fever, and inflammation and pharmaceutical compositions for use therein, wherein the active ingredient comprises a compound of the formula:

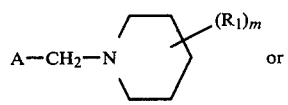

or (I.)

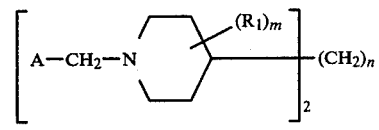

(II.)

wherein A and $R_1$ represent various substituents.

18 Claims, No Drawings

TREATMENT OF PAIN, FEVER, AND INFLAMMATION WITH COMPOSITIONS CONTAINING 2-(SUBSTITUTEDPIPERIDINOMETHYL)PROPANE AND PROPENE NITRILES

BACKGROUND OF THE INVENTION

1. Field of the Invention

The present invention is concerned with a novel method of treating pain, fever, and inflammation and novel compositions for use therein containing as an active ingredient, a 2-(substitutedpiperidinomethyl)propane-or propene nitrile compound.

2. Brief Description of the Prior Art

Various 2-(substitutedpiperidinomethyl)propane and propene nitriles used in the method and compositions of the present invention are disclosed in Dybas et al, Developments in Industrial Microbiology, Vol. 19, pp. 347–353 (1978). However, they are described therein as being useful in a process for protecting materials of various kinds against infection and damage by microorganisms, as by bacteria and fungi, and, thus, the method of treatment and compositions of the present invention are not suggested.

SUMMARY OF THE INVENTION

In accordance with the present invention, there is also provided a method of treating pain, fever, and inflammation comprising administering to a host in need of such treatment a therapeutically effective amount of a compound of the formula:

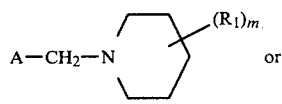

(I.)

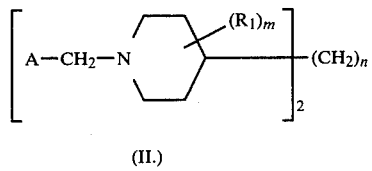

(II.)

wherein
A is

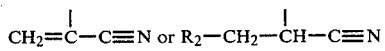

where $R_2$ is selected from amino; $C_{1-18}$ alkyl and hydroxy substituted $C_{1-18}$ alkyl N-mono- and N,N-disubstitutedamino; hydroxy; $C_{1-8}$ alkoxy; piperidino; and substituted piperidino of the formula:

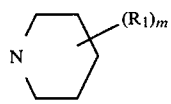

where $R_1$ and m are as defined below;
$R_1$ is selected from $C_{1-8}$ alkyl; $C_{2-8}$ alkenyl; $C_{3-12}$ aliheterocyclic; $C_{3-12}$ alicyclic $C_{1-3}$ alkyl; hetero $C_{5-6}$ alicyclic $C_{1-3}$ alkyl where the single hetero atom is nitrogen or oxygen; aryl; aryl $C_{1-3}$ alkyl; carboxyl; hydrogen sulfito; $C_{1-4}$ alkoxycarbonyl; $C_{1-4}$ alkylcarbonyl; carbamyl; halo; cyano; trifluoromethyl; formyl; hydroxy; hydroxy $C_{1-3}$ alkyl; and $C_{1-4}$ alkyl N-mono- and N,N-disubstitutedcarbonylamino;

m is 0 to 4; and
n is 0 to 3;

and acid addition and quaternary salts thereof.

Examples of preferred compounds for use in the novel pharmaceutical compositions and method of treatment of the present invention are:
2-(4-carbamylpiperidinomethyl)propenenitrile
2-(4-carboxypiperidinomethyl)propenenitrile
2-[4-(N-butylcarbamyl)piperidinomethyl]-propenenitrile
2-(1-piperidinomethyl)propenenitrile 2-(4-hydroxypiperidinomethyl)propenenitrile
2-(3-hydroxymethylpiperidinomethyl)propenenitrile
2-(4-ethoxycarbonylpiperidinomethyl)propenenitrile
2-[4-(1-piperidinyl)-1-piperidinomethyl]propenenitrile
2-(4-cyclohexylmethylpiperidinomethyl)propenenitrile
2-(2-methylpiperidinomethyl)propenenitrile
2-(4-t-butylpiperidinomethyl)propenenitrile
2-(4-hydroxy-4-phenylpiperidinomethyl)-propenenitrile
4,4'-(1,3-propanediyl)bis-β-methylene-1-piperidinepropanenitrile The present invention also provides pharmaceutical compositions for treating a condition exhibiting at least one of the symptoms of pain, fever, and inflammation, comprising a pharmaceutically acceptable, non-toxic carrier, and a therapeutically effective amount of a compound of Formulas I or II, as described above.

The propenenitrile derivatives are synthesized as follows:

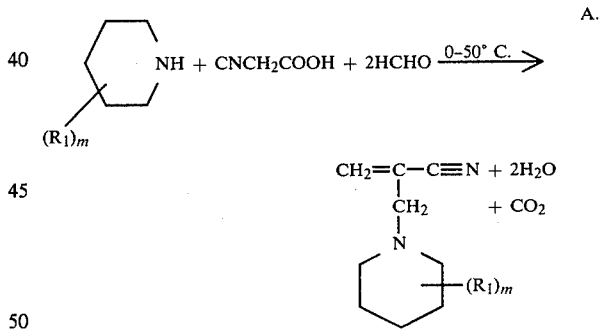

A.

The 2-cyano-1,3-disubstituted propanes are obtained by nucleophilic addition:

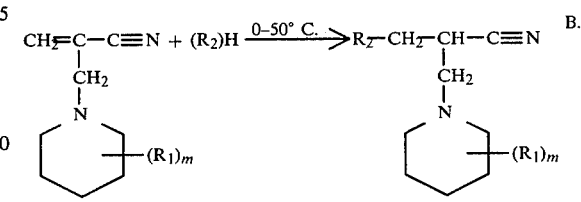

B.

where $R_1$, $R_2$ and m are as previously defined.

Substituted piperidines are available chemically by a variety of methods. An extensive review of such procedures may be found in *Heterocyclic Compounds*, V. I, R. C. Elderfield, Editor, John Wiley and Sons, Inc., New York (1950), p. 631–676. Pyridine compounds may be reduced to the piperidines with sodium in lower alkanols, with tin and hydrochloric acid or by catalytic hydrogenation with nickel or noble metal catalysts. Generally, the pyridines substituted with a variety of groups are more easily reduced then the unsubstituted pyridine.

4-Hydroxypiperidine can be prepared according to the method of E. E. Mikhlina, V. Ya. Vorobeva and M. V. Rubtsov [*Zhur. Obschei Khim.* 30 18885-93 (1960)] by the reduction of 4-piperidone hydrochloride with sodium borohydride in ethyl alcohol using ice cooling in 61% yield.

Various alkyl substituted piperidines can be synthesized following the procedures of J. LaKomy, A. Silhankova, M. Ferles and O. Exner [*Collection Czechoslov. Chem. Commun.*, 33, 1700–1708 (1968)]. 3-Isopropylpiperidine was prepared by the sodium reduction of 3-isopropylpyridine in boiling ethyl alcohol; 4-isopropylpiperidine by the electrolytic reduction of dimethyl-4-pyridylcarbinol and subsequent catalytic hydrogenation with Adams platinum; cis and trans-2,4-dimethylpiperidine from the sodium reduction in butyl alcohol of 2,4lutidine. Many polyalkylated pyridines are commercially available either from coal tar or by total synthesis. The compounds are readily converted to the corresponding piperidines using either chemical or catalytic reduction methods well known in the art.

4-Chloropiperidine is obtained from 4-hydroxypiperidine by reaction with supersaturated hydrochloric acid for 12 hours at 140° C. according to the method of R. Fankhauser, C. A. Grob and V. Krasnobajew, [*Helv. Chim. Acta.*, 49, 690–695 (1966)]. 4-Chloro-2,2,6,6-tetramethylpiperidine is obtained similarly from the 4-hydroxy derivative. Hydrogenation of triacetone amine in ethyl alcohol with Adams platinum catalyst provides the tetramethylated hydroxypiperidine.

2,5-Dimethyl-4-piperidinol and 2,5-dimethyl-4-ethyl-4-piperidinol may be prepared according to the methods of I. N. Nazarov, A. S. Shatif Kanov, S. A. Yasupov and T. G. Sarbaev [*Zhur. Obschei Khim.*, 30, 3267–71 (1960)].

Generally, the reaction as illustrated by equation A. is run using equimolar quantities of a substituted piperidine and cyanoacetic acid with two moles or more of formaldehyde in homogeneous solution such as with dioxane. The initiation of product formation, usually beginning after 15 minutes is marked by evolution of carbon dioxide and completion obtained after three hours. Occasionally, reaction times as long as 30 hours at 25° C.–35° C. are required for total conversion. It is useful for good control to precool the cyanoacetic acid in dioxane solution to 5° C.–15° C., gradually add the piperidine derivative with the cold bath applied and finally the formaldehyde. After all has been added, the ice bath is removed and the solution allowed to warm.

The work-up involves stripping off the solvent at 40° C./15 mm., taking up the residue in ether and washing with cold aqueous 5% potassium carbonate followed by ice water. The ether solution is then dried over anhydrous magnesium sulfate, filtered and volatiles removed to an internal temperature of 40° C.–50° C. at 15 mm. The residue is further purified preferably by fractional distillation under reduced pressure. Often, the quality is sufficiently high to permit use as isolated.

The 2-cyano-1,3-disubstituted propanes are prepared in accordance with the chemical scheme of equation B. For those products in which the substituted piperidino groups at the 1 and 3 carbon atoms of the 2-cyanopropanes are identical, a change in molar reactant ratios from 1 mole of ring substituted piperidine to 2 moles per mole of cyanoacetic acid and per 2 moles of formaldehyde will provide the compounds in one process step.

The sequence of steps may be postulated as depicted by equations A. and B., wherein $(R_2)H$ is simply the second mole of

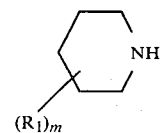

where $R_1$, $R_2$, and m are as above defined. When $(R_2)H$ is to be different, then the unsaturated nitrile products of equation A. may be dissolved in dioxane, mixed with a 5–25% molar excess of the compound $(R_2)H$, which may be previously dissolved in the same volume of water or dioxane, and allowed to stand at 20° C.–35° C. until addition is complete. Disappearance of the double bond, as measured by a change in infrared absorption or loss of the vinyl protons in the nucelar magnetic reasonance spectrum, is used to monitor the progress of the reaction. Dry, powdered potassium carbonate is then added to saturation and the mixture extracted with ether. After filtration of the separated organic phase and drying over anhydrous magnesium sulfate, the solvent is stripped and the residue purified by fractional distillation under reduced pressure.

Both Formula I and Formula II compounds can be used in the form of salts derived from inorganic or organic acids. Included among such salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates; long chain halides such as decyl, lauryl, myristyl and stearyl chlorides, bromides and iodides, aralkyl halides like benzyl and phenethyl bromides and others. Water or oil-soluble or dispersible products are thereby obtained.

The 2-(substitutedpiperidinomethyl)propane and propene nitriles of the present invention possess a high degree of anti-inflammatory, analgesic and anti-pyretic activity. They are of value in the treatment of arthritic and dermatological disorders or like conditions responsive to anti-inflammatory drugs. In general they are indicated for a wide variety of conditions where one or more of the symptoms of inflammation, fever and pain are manifested. Included within this category are diseases such as rheumatoid arthritis, osteo arthritis, gout, infectious arthritis and rheumatic fever. As indicated above the compounds utilized in the practice of the invention also possess a useful degree of analgesic and anti-pyretic activity.

For these purposes the compounds of the present invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide a pharmaceutically elegant and palatable preparation. Tablets contain the active ingredient in admixture with non-toxic pharmaceutically acceptable excipients which are suitable for manufacture of tablets. These excipients may be, for example, inert diluents, such as calcium carbonate, sodium carbonate, lactose, calcium phosphate or sodium phosphate; granulating and disintegrating agents, for example maize starch, or alginic acid; binding agents, for example starch, gelatine or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate alone or with a wax may be employed.

Formulations for oral use may also be presented as hard gelatine capsules wherein the active ingredient is mixed with an inert solid diluent, for example calcium carbonate, calcium phosphate or kaolin, or as soft gelatine capsules wherein the active ingredient is mixed with water or an oil medium, for example arachis oil, peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a natural-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol mono-oleate, or condensation products of ethylene oxide with partial esters derived from fatty acids and hexitol anhydrides, for example polyoxyethylene sorbitan mono-oleate. The said aqueous suspensions may also contain one or more preservatives, for example, ethyl or n-propyl p-hydroxy benzoate, one or more coloring agents, one or more flavoring agents and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oil suspensions may contain a thickening agent, for example beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally-occurring phosphatides, for example soya bean lecithin, and esters or partial esters derived from fatty acids and hexitol anhydrides, for example sorbitan mono-oleate, and condensation products of the said partial esters with ethylene oxide, for example polyoxyethylene sorbitan mono-oleate. The emulsions may also contain sweetening and flavoring agents.

Syrups and elixirs may be formulated with sweetening agents, for example glycerol, sorbitol or sucrose. Such formulations may also contain a demulcent, a preservative and flavouring and colouring agents. The pharmaceutical compositions may be in the form of a sterile injectable preparation, for example as a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectibles.

The compounds of this invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc. containing the antiinflammatory agents are employed.

Dosage levels of the order of .20 mg. to 1 gram per day are useful in the treatment of the above indicated conditions. For example, inflammation is effectively treated and anti-pyretic and analgesic activity manifested by the administration of from about 0.3 to 60 milligrams of the compound per kilogram of body weight per day. Advantageously from about 2 mg. to about 30 mg. per kilogram of body weight and especially from about 4 mg. to about 20 mg./kg. per daily dosage produce highly effective results.

The amount of active ingredient that may be combined with the carrier materials to produce a single dosage form will vary depending upon the host treated and the particular mode of administration. For example, a formulation intended for the oral administration of humans may contain from 5 mg. to 1 gram of active agent compounded with an appropriate and convenient amount of carrier material which may vary from about 5 to about 95 percent of the total composition. Dosage-unit forms will generally contain between from about 25 mg. to about 500 mg. of active ingredient.

It will be understood, however, that the specific dose level for any particular patient will depend upon a variety of factors including the activity of the specific ompound employed, the age, body weight, general health, sex, diet, time of administration, route of administration, rate of excretion, drug combination and the severity of the particular disease undergoing therapy.

The following examples will serve to illustrate preparation of the compounds used in the method of treatment and pharmaceutical compositions of the present invention, without, however, limiting the scope thereof.

EXAMPLE 1

2-(1-Piperidylmethyl)propenenitrile

Cyanoacetic acid (51 g., 6 mole) was dissolved in 150 ml. of dioxane, the solution cooled to 5° C. and piperidine (53 g., 0.6 mole) dripped in while maintaining the temperature at 10°-15° C. Then, 37% aqueous formaldehyde (109.5 g., 1.35 mole) was slowly added at 0°-10° C. After two hours, the ice bath was removed and the mixture stirred overnight at 20°-25° C. It was then stripped at 15 mm. pressure and bath temperature of 48° C. The residue was chilled, mixed with 100 ml. of ether, saturated with sodium chloride and the ether layer separated. This extract was washed with two 25 ml. portions of cold 5% aqueous potassium carbonate and finally with 10 ml. of ice water. The ether solution was dried over anhydrous magnesium sulfate, filtered, stripped and fractionated using a Vigreux column. The fraction boiling at 86° -88°C./2 mm. was of practically analytical quality, 40.8 g., $R_f$ 0.66 on silica gel using chloroform-methyl alcohol (90:10) development. This is, however, a known compound.

EXAMPLE 2

2-(4-Fluoro-1-piperidylmethyl)propenenitrile

4-Fluoropiperidine (0.7 g., 0.005 mole) was dissolved in a mixture of 3 ml. of dioxane and 2 ml. of water containing cyanoacetic acid (0.43 g., 0.005 mole). Then, 0.85 g. (0.01 mole) of 37% aqueous formaldehyde was added to the solution. The solution was heated to 65° C. and carbon dioxide evolution began. It was maintained at 60°-65° C. for 2½ hours and allowed to stand overnight. A solid gummy residue, 1 gm., was obtained upon stripping in a bath at 55° C. and at 1 mm. It was taken up in a small amount of water, made alkaline with sodium bicarbonate and extracted with ether. The organic layer was water washed and dried over anhydrous sodium sulfate. After solvent stripping, the product was obtained as a colorless oil, 0.7 g., of analytical purity.

EXAMPLE 3

2-(4-Hydroxy-1-piperidylmethyl)propenenitrile

Cyanoacetic acid (8.5 g., 0.1 mole) was dissolved in 25 ml. of dioxane. 4-Hydroxypiperidine (10.1 g., 0.1 mole) was added within two minutes; the resultant slurry temperature rose to 33° C. After 1 hour of mixing, 37% aqueous formaldehyde (17 g., 0.2 mole) was run in over a 12 minute period. The temperature rose to 38° C. and carbon dioxide evolved steadily. All was in solution after about one-half of the formaldehyde was added and an additional twelve hours was used to complete the reaction. It was then stripped using a bath at 46° C. and 1-5 mm. of pressure. The residual oil, 17 g., was taken up in methylene chloride, washed with water, dried and stripped to leave 8.1 g. of nearly colorless product, b.p. 125° C./1 mm.

Methiodide Quaternary salt of 2-(4-hydroxy-1-piperidylmethyl)propenenitrile

The title base (1.66 g., 0.01 mole) was dissolved in 25 ml. of dry ether and mixed with 0.7 ml. methyl iodide. On stirring overnight, a yellow oily film was evident. An additional 1.0 ml. of methyl iodide was added and reacted overnight. A solid formed which after removal of ether by decantation and further ether washing was dried under vacuum; yield, 1.5 g. of a pale yellow solid m.p. 169°-173° C. with decomposition. It is non-hygroscopic and analytically pure.

Benzyl Bromide Quaternary Salt of 2-(4-Hydroxy-1-piperidylmethyl)propenenitrile 2-(4-Hydroxy-1-piperidylmethyl)propenenitrile (1.66 g., 0.01 mole) was dissolved in 15 ml. of acetone and mixed with benzyl bromide (1.9 g., 0.011 mole). The solution was heated in a bath at 70° C. for 12 hours, a white precipitate formed. The product was washed with acetone followed by ether and then dried at 45° C. under vacuum; yield, 2.8 g., m.p. 183°-185.5° C.

Other quaternary salts may be synthesized using n-butyl bromide, n-dodecyl chloride, 2-ethylhexyl bromide, hexadecyl bromide, phenethyl bromide following this procedure.

Acid salts such as the hydrochloride, sulfate, phosphate, nitrate, bromide are obtained simply upon the addition of aqueous solution in slight theoretical excess to aqueous alcohol solutions of the free base substituted piperidinomethyl propene and propane nitriles. The salts can be isolated by removing the solvents at ambient temperature and under reduced pressure or generally by precipitation using acetone. The anion such as chloride, bromide, or nitrate may be exchanged for dodecylbenzene sulfonate, laurylether sulfate and the like by metathetical reaction with the sodium salt in aqueous alcohol. Alternatively, ion exchange using resins, a well known technique, may also be employed.

EXAMPLE 4

2-[(-3-Hydroxymethyl-1-piperidyl)methyl])propenenitrile

Cyanoacetic acid (25.5 g., 0.3 mole) was dissolved in 75 ml. of dioxane, cooled to 0°–10° C., and with the cooling bath in place, 3-piperidinemethanol (34.5 g., 0.3 mole) dripped in. The temperature then rose upon the addition of 37% aqueous formaldehyde (50 g., 0.6 mole) to 30° C. with the cold bath removed. After mixing overnight at room temperature, the mixture was concentrated in a rotary evaporator, saturated with sodium chloride and extracted with ether. The organic phase was washed with sodium carbonate solution, dried and concentrated. The residue yielded 43.8 g.; 38 g. was fractionally distilled and the product isolated, 22.4 g., b.p. 137° C./0.4 mm.

EXAMPLE 5

2-[(4-t-Butyl-1-piperidyl)methyl]propenenitrile

Cyanoacetic acid (1.75 g., 0.02 mole) was dissolved in 10 ml. of dioxane. In a five minute period 4-t-butylpiperidine (2.8 g., 0.02 mole) was added, the temperature rose to 25° C. from 15° C. obtained by prior cooling with an ice bath. The mixture which solidified became fluid upon the addition of 37% aqueous formaldehyde (3.6 g., 0.04 mole), the temperature rose to 30° C. and carbon dioxide evolution began. The mixture was stirred an additional 12 hours, was taken up in ether and the organic phase separated and washed with water. The dried ether solution was stripped of solvent to leave a solid residue product, 3.7 g. of practically analytical purity.

EXAMPLE 6

2-[(4-Cyclohexylmethyl-1-piperidyl)methyl]propenenitrile

Cyanoacetic acid (0.9 g., 0.01 mole) was dissolved in 6 ml. of dioxane and 1 ml. of water. In a 15 minute period, 4-cyclohexylmethylpiperidine (1.8 g., 0.01 mole) was added. After an additional 15 minutes, 37% aqueous formaldehyde (1.8 g., 0.02 mole) was dripped in over a two minute period. The reaction mixture was agitated twelve hours at 20°–25° C., extracted with 200 ml. of ether, water washed, dried over anhydrous sodium sulfate, filtered and stripped. A yield of 1.2 g. of high purity product was obtained as a residue.

EXAMPLE 7

2-[(4-Hydroxy-4-phenyl-1-piperidyl)methyl]propenenitrile

A solution of cyanoacetic acid (4.3 g., 0.05 mole) in 15 ml. of dioxane was cooled with an ice bath, and 4-hydroxy-4-phenylpiperidine (8.8 g., 0.05 mole) added while maintaining an internal temperature of 20°–25° C. Upon complete addition and a further fifteen minutes of stirring 37% aqueous formaldehyde (9 gm., 0.10 mole) was added dropwise in approximately five minutes. When approximately half was added carbon dioxide evolution was observed, the maximum internal temperature was 28° C. The reaction mixture was stirred overnight, mixed with 100 ml. of methylene chloride, the organic phase separated washed with water and salt solution. Upon removal of solvent the product was obtained as an oil, 10.5 g., in practically analytical purity.

EXAMPLE 8

1-(2-Cyano-2-propenyl)-4-piperidinecarboxamide

Cyanoacetic (9 g., 0.1 mole) was dissolved in 30 ml. of dioxane and 5 ml. of water. Isonipecotamide (12.8 g., 0.1 mole) was then added followed by an additional 10 ml. of water to provide nearly total dissolution. Finally, 37% aqueous formaldehyde (18 g., 0.22 mole) was added within three minutes and the internal temperature rose to 35° C.; vigorous gassing ensued. The reaction mixture was stirred twelve hours and then stripped using a rotary evaporator at 15 mm. pressure. The solid residue was taken up in 100 ml. of methylene chloride, washed with 100 ml. of water, dried over anhydrous magnesium sulfate, and then stripped to a solid residue, 7.5 g., m.p. 127°–129° C., which was analytically pure.

EXAMPLE 9

N-(n-Butyl)-1-(2-cyano-2-propenyl)-4-piperidinecarboxamide

Cyanoacetic acid (0.9 g., 0.01 mole) was dissolved in 11 ml. of dioxane and 4 ml. of water. N-Butyl isonipecotamide (1.84 g., 0.01 mole) was added with stirring in portions to keep the temperature below 30° C. In 2 minutes 37% aqueous formaldehyde (1.66 g., 0.02 mole) was added and the temperature maintained at 25°–28° C. Carbon dioxide evolution was evident. After 4 hours, the reaction appeared complete as determined by thin layer chromatography on silica gel developed with chloroform-methyl alcohol (95:5). The solvents were removed by stripping at 35° C./15 mm. and the residue taken up in 100 ml. methylene chloride. The organic phase was washed with water, dried and stripped to yield 1.7 g. of product, analytically pure.

EXAMPLE 10

2-[4-(1-Piperidylmethyl)-1-piperidyl]methyl propenenitrile 4-(1-Piperidylmethyl)piperidine (0.05 mole) was dissolved in 17 ml. of dioxane containing cyanoacetic acid (4.25 g., 0.05 mole) by warming and the solution then cooled to 22° C. Over a 9 minute period, 37% aqueous formaldehyde (8.5 g., 0.1 mole) was dripped in. The temperature throughout the addition was 25°–28° C. It was then warmed to 35°–40° C. for carbon dioxide evolution and maintained then for 2 hours. The mixture was stripped at a bath temperature of 60° C./15 mm. to leave approximately 12 g. of an oil. Most dissolved in 150 ml. of ether; the solution was washed twice with water, dried over anhydrous sodium sulfate and the solvent stripped. A nearly colorless oil was obtained, 8.6 g., which gradually solidified on standing at room temperature.

EXAMPLE 11

2-4,4'-(1,3-Propanediyl)bis-β-methylene-1-piperidinopropanenitrile

Cyanoacetic acid (8.5 g., 0.1 mole) was dissolved in 45 ml. of dioxane. The 4,4'-trimethylenedipiperidine (10.5 g., 0.005 mole) was added. The temperature rose to 31° C. with precipitation of the salt. Partial solution was obtained by the addition of 10 ml. of water. In 10 minutes, 37% aqueous formaldehyde (18 g., 0.2 mole) was dripped in. The exotherm resulted in a temperature climb to 41° C. The two phase reaction mixture was stirred an additional 12 hours at 25°–30° C. The mixture was concentrated to a solid residue by stripping under vacuum. It was mixed with ether, washed with water and the organic phase dried over anhydrous sodium sulfate. The filtered solution was stripped using a bath temperature of 40°-43° C. and 1 mm. finally. The residue crystallized on cooling to room temperature; yield, 16.4 g.

EXAMPLE 12

2-(4-Carboxy-1-piperidylmethyl)propenenitrile

Cyanoacetic acid (12.8 g. 0.15 mole) was dissolved in 25 ml. of dioxane. Next, isonipecotic acid (19.4 g., 0.15 mole) was added. Then, 37% aqueous formaldehyde (25 g., 0.3 mole) was dripped in and the temperature maintained at a maximum of 35° C. After mixing overnight sodium chloride was added to saturation and methylene chloride used to extract the mixture. The organic phase was washed with water, dried over anhydrous sodium sulfate and after filtration, concentrated. Most of the product appeared in the aqueous phase. This was extracted twice with 500 ml. of methylene chloride in a continuous extractor. The residue obtained after solvent removal weighed 14.2 g., m.p. 109°-111° C. of analytical purity.

EXAMPLE 13

2-(4-Carboethoxy-1-piperidylmethyl)propenenitrile

Cyanoacetic acid (8.6 g., 0.1 mole) was dissolved in 35 ml. of dioxane. 4-Carboethoxypiperidine (15.7 g., 0.1 mole) was added—a precipitate rapidly formed. When one-half was added 10 ml. of water was then admixed and the temperature controlled below 24° C. until complete addition. With ice bath cooling, 37% aqueous formaldehyde (18 g., 0.2 mole) was dripped in over an 8-minute period and the temperature allowed to rise to 29° C. accompanied by vigorous carbon dioxide evolution. Two phases separated and stirring was continued for an additional 12 hours. After concentration in a bath at 45° C. and under reduced pressure, 22.4 g. of an oil resulted. The product was distilled, b.p., 130°-132° C./0.6 mm., yield, 16.3 g.

EXAMPLE 14

2-Cyano-1-dimethylamino-3-(4-hydroxypiperidino)propane

2-Dimethylaminomethylpropenenitrile (1.1 g., 0.01 mole) was cooled to 10°-15° C. and to it was added dropwise 4-hydroxypiperidine (1.0 g., 0.01 mole). The evolution of heat is observed. The homogeneous mixture is allowed to stand 12 hours at 15°-20° C. Completion of addition reaction is determined using thin layer chromatography on silica gel with benzene-methyl alcohol (90:10) development. The appearance of a single spot and elimination of reactant spots indicate termination.

Similarly, 2-hydroxymethylpropenenitrile, 2-piperidinomethylpropenenitrile, 2-(4-hydroxypiperidino)-propenenitrile, 2-aminomethylpropenenitrile, 2-methylaminomethylpropenenitrile, 2-methoxymethylpropenenitrile and other $R_2$ containing 3-substituted-2-methylenepropanenitriles may be used for the addition reaction with substituted piperidines as defined by

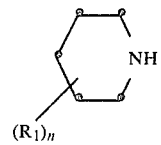

Generally, equimolar quantities of reactants are employed as illustrated without solvent and at 10°-25° C. Inert solvents which are suitable may be water, dioxane, methylene chloride, isopropyl alcohol and mixtures of these. It is also possible to use as reactants the propenenitriles of this invention and add the $(R_2)H$ reactant as defined following the conditions outlined in this example.

EXAMPLE 15

A mixture of 250 parts of 2-(4-carbamylpiperidinomethyl)propenenitrile dihydrochloride and 25 parts of lactose is granulated with suitable water, and to this is added 100 parts of maize starch. The mass is passed through a 16 mesh screen. The granules are dried at a temperature below 60° C. The dry granules are passed through a 16 mesh screen and mixed with 3.8 parts of magnesium stearate. They are then compressed into tablets suitable for oral administration.

The compound used in the foregoing example may be replaced by 25, 100, 250, or 500 parts of the propenenitrile to produce tablets suitable for oral administration as an anti-inflammatory, antipyretic and/or analgesic according to the method of this invention.

EXAMPLE 16

A mixture of 50 parts of 2-(4-carboxypiperidinomethyl)propenenitrile pamoate, 3 parts of the calcium salt of lignin sulphonic acid, and 237 parts of water is ball-milled until the size of substantially all particles of the compound is less than 10 microns. The suspension is diluted with a solution containing 3 parts of sodium carboxymethylcellulose and 0.9 parts of the butyl ester of p-hydroxybenzoic acid in 300 parts of water. There is thus obtained an aqueous suspension suitable for oral administration for therapeutic purposes.

EXAMPLE 17

A mixture of 250 parts of 2-(1-piperidinomethyl)-propenenitrile succinate, 200 parts of maize starch and 30 parts of alginic acid is mixed with a sufficient quantity of a 10% aqueous paste of maize starch, and granulated. The granules are dried in a current of warm air and the dry granules are then passed through a 16-mesh screen, mixed with 6 parts of magnesium stearate and compressed into tablet form to obtain tablets suitable for oral administration.

EXAMPLE 18

A mixture of 500 parts 2-(4-hydroxypiperidinomethyl)propenenitrile hydrochloride, 60 parts maize starch and 20 parts of gum acacia is granulated with a sufficient quantity of water. The mass is passed through a 12-mesh screen and the granules are dried in a current of warm air. The dry granules are passed through a 16-mesh screen, mixed with 5 parts of magnesium stearate and compressed into tablet form suitable for oral administration.

EXAMPLE 19

(1) Tablets—10,000 scored tablets for oral use, each containing 100 mg. of propenenitrile, are prepared from the following ingredients.

|  | Gm. |
| --- | --- |
| 2-(3-hydroxymethylpiperidinomethyl)-propenenitrile adipate | 1000 |
| Starch, U.S.P. | 350 |
| Talc, U.S.P. | 250 |
| Calcium Stearate | 35 |

The powdered adipate salt is granulated with a 4% w./v. aqueous solution of methylcellulose U.S.P. (1500 cps.). To the dried granules is added a mixture of the remainder of the ingredients and the final mixture compressed into tablets of proper weight.

(2) Capsules—10,000 two-piece hard gelatin capsules for oral use, each containing 50 mg. of the propenenitrile adipate are prepared from the following ingredients:

|  | Gm. |
| --- | --- |
| 2-(3-hydroxymethylpiperidinomethyl)-propenenitrile adipate | 500 |
| Lactose, U.S.P. | 1000 |
| Starch, U.S.P. | 300 |
| Talc, U.S.P. | 65 |
| Calcium Stearate | 25 |

The powdered adipate salt is mixed with the starch-lactose mixture followed by the talc and calcium stearate. The final mixture is then encapsulated in the usual manner. Capsules containing 10 and 25 mg. of the adipate salt are also prepared by substituting 100 and 250 gm. for 500 gm. in the above formulation.

(3) Soft elastic capsules—One piece soft elastic capsules for oral use, each containing 50 mg. of 2-(3-hydroxymethylpiperidinomethyl)propenenitrile adipate are prepared in the usual manner by first dispersing the powdered active material in sufficient corn oil to render the material capsulatable.

(4) Aqueous suspension—An aqueous suspension for oral use containing in each 5 ml., 200 mg. of propenenitrile is prepared from the following ingredients:

|  | Gm. |
| --- | --- |
| 2-(3-hydroxymethylpiperidinomethyl)-propenenitrile | 400 |
| Methylparaben, U.S.P. | 7.5 |
| Propylparaben, U.S.P. | 2.5 |
| Saccharin sodium | 12.5 |
| Glycerin, 3000 ml. | 12.5 |
| Tragacanth Powder | 10 |
| Orange Oil Flavor | 10 |
| F.D. and C. Orange Dye | 7.5 |
| Deionized Water, q.s. to 10,000 gm. | |

What is claimed is:

1. A method of treating a condition exhibiting at least one of the symptoms of pain, fever, and inflammation, comprising administering to a patient in need of such treatment a therapeutically effective amount of a compound of the formula:

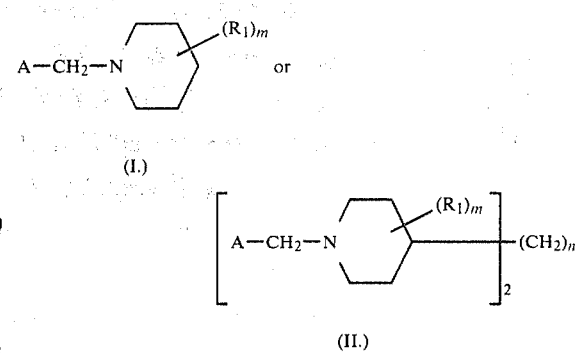

wherein
A is

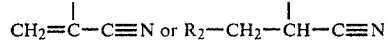

where $R_2$ is selected from amino; $C_{1-4}$ alkyl N-mono- and N,N-disubstitutedamino; hydroxy; $C_{1-8}$ alkoxy; piperidino; and substituted piperidino of the formula:

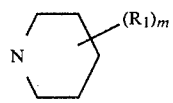

where $R_1$ and m are as defined below;
$R_1$ is selected from $C_{1-8}$ alkyl; $C_{2-8}$ alkenyl; $C_{3-12}$ aliheterocyclic; $C_{3-12}$ alicyclic $C_{1-3}$ alkyl; hetero $C_{5-6}$ alicyclic $C_{1-3}$ alkyl where the single hetero atom is nitrogen or oxygen; aryl; aryl $C_{1-3}$ alkyl; carboxyl; hydrogen sulfito; $C_{1-4}$ alkoxycarbonyl; $C_{1-4}$ alkylcarbonyl; carbamyl; halo; cyano; trifluoromethyl; formyl; hydroxy; hydroxy $C_{1-3}$ alkyl; and $C_{1-4}$ alkyl N-mono- and N,N-disubstitutedcarbonylamino;
m is 0 to 4; and
n is 0 to 3;
and acid addition and quaternary salts thereof.

2. The method of claim 1 wherein the compound is 2-(4-carbamylpiperidinomethyl)propenenitrile.

3. The method of claim 1 wherein the compound is 2-(4-carboxypiperidinomethyl)propenenitrile.

4. The method of claim 1 wherein the compound is 2-(1-piperidinomethyl)propenenitrile.

5. The method of claim 1 wherein the compound is 2-(4-hydroxypiperidinomethyl)propenenitrile.

6. The method of claim 1 wherein the compound is 2-(3-hydroxymethylpiperidinomethyl)propenenitrile.

7. The method of claim 1 wherein the compound is 2-(4-ethoxycarbonylpiperidinomethyl)propenenitrile.

8. The method of claim 1 wherein the compound is 2-(2-methylpiperidinomethyl)propenenitrile.

9. The method of claim 1 wherein the compound is 4,4'-(1,3-propanediyl)bis-β-methylene-1-piperidinopropanenitrile.

10. A pharmaceutical composition for treating a condition exhibiting at least one of the symptoms of pain, fever, and inflammation, in unit dosage form suitable for oral administration selected from the group consisting of tablets, oily suspensions, soft and hard gelatin capsules, syrups, and elixers, comprising a pharmaceutically acceptable, non-toxic carrier, containing one or more agents selected from the group consisting of sweetening agents, flavoring agents, coloring agents, and preserving agents, and a therapeutically effective amount of a compound of the formula:

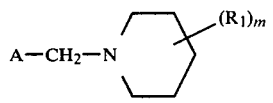  (I.)

or

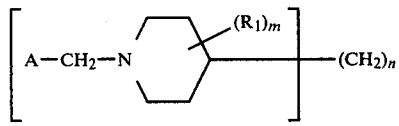  (II.)

wherein

A is

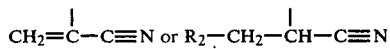

where $R_2$ is selected from amino; $C_{1-4}$ alkyl N-mono- and N,N-disubstitutedamino; hydroxy; $C_{1-8}$ alkoxy; piperidino; and substituted piperidino of the formula:

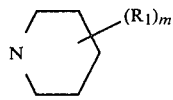

where $R_1$ and m are as defined below:

$R_1$ is selected from $C_{1-8}$ alkyl; $C_{2-8}$ alkenyl; $C_{3-12}$ aliheterocyclic; $C_{3-12}$ alicyclic $C_{1-3}$ alkyl; hetero $C_{5-6}$ alicyclic $C_{1-3}$ alkyl where the single hetero atom is nitrogen or oxygen; aryl; and aryl $C_{1-3}$ alkyl; carboxyl; hydrogen sulfito; $C_{1-4}$ alkoxycarbonyl; $C_{1-4}$ alkylcarbonyl; carbamyl; halo; cyano; trifluoromethyl; formyl; hydroxy; hydroxy $C_{1-3}$ alkyl; and $C_{1-4}$ alkyl N-mono- and N,N-disubstitutedcarbonylamino;

m is 0 to 4; and n is 0 to 3;

and acid addition and quaternary salts thereof.

11. The composition of claim 10 wherein the compound is 2-(4-carbamylpiperidinomethyl)propenenitrile.

12. The composition of claim 10 wherein the compound is 2-(4-carboxypiperidinomethyl)propenenitrile.

13. The composition of claim 10 wherein the compound is 2-(1-piperidinomethyl)propenenitrile.

14. The composition of claim 10 wherein the compound is 2-(4-hydroxypiperidinomethyl)propenenitrile.

15. The composition of claim 10 wherein the compound is 2-(3-hydroxymethylpiperidinomethyl)propenenitrile.

16. The composition of claim 10 wherein the compound is 2-(4-ethoxycarbonylpiperidinomethyl)propenenitrile.

17. The composition of claim 10 wherein the compound is 2-(2-methylpiperidinomethyl)propenenitrile.

18. The composition of claim 10 wherein the compound is 4,4'-(1,3-propanediyl)bis-β-methylene-1-piperidinopropanenitrile.

* * * * *